United States Patent [19]

Pilgram

[11] Patent Number: 4,493,728

[45] Date of Patent: Jan. 15, 1985

[54] PLANT GROWTH INHIBITING OXAZOLYL-SUBSTITUTED TRIAZINONE AND OXADIAZINONE DERIVATIVES, COMPOSITIONS, AND METHOD OF USE

[75] Inventor: Kurt H. Pilgram, Modesto, Calif.

[73] Assignee: Shell Oil Company, Houston, Tex.

[21] Appl. No.: 507,874

[22] Filed: Jun. 27, 1983

[51] Int. Cl.$^3$ .................... A01N 43/64; A01N 43/88; C07D 413/04

[52] U.S. Cl. ............................ 71/92; 71/93; 424/248.4; 424/249; 544/67; 544/216; 544/220

[58] Field of Search ................... 544/67, 216, 220; 424/248.4, 249; 71/92, 93

[56] References Cited

U.S. PATENT DOCUMENTS 3,994,997 11/1976 Singerman ..................... 260/944
4,062,861 12/1977 Yukinaga et al. ............. 260/307 H

FOREIGN PATENT DOCUMENTS 2014992 9/1979 United Kingdom ................ 71/92

Primary Examiner—Henry R. Jiles
Assistant Examiner—J. G. Mullins

[57] ABSTRACT

Hexahydrotriazinones substituted by a 5-substituted-1,2-oxazol-3-yl moiety, useful for controlling the growth of unwanted plants.

7 Claims, No Drawings

PLANT GROWTH INHIBITING OXAZOLYL-SUBSTITUTED TRIAZINONE AND OXADIAZINONE DERIVATIVES, COMPOSITIONS, AND METHOD OF USE

DESCRIPTION OF THE INVENTION

It has been found that the growth of certain plants is adversely affected by compounds of the formula:

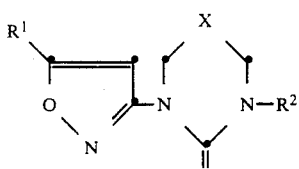
(I)

wherein $R^1$ contains from three to five carbon atoms and is one of alkyl, alkenyl, alkynyl, alkoxyalkyl, alkylthioalkyl, alkylsulfinylalkyl, alkylsulfonylalkyl, cycloalkyl, and alkylcycloalkyl, $R^2$ is alkyl, alkoxy, (mono- or polyhalo)alkyl of from one to three carbon atoms, cycloalkyl of from three to six carbon atoms, or alkenyl of from three to five carbon atoms, and X is —O— or

wherein $R^3$ is alkyl of from one to three carbon atoms, cyclopropyl or 1-methylcyclopropyl.

In these compounds, each alkyl, alkoxy, alkenyl and alkynyl moiety suitably is either straight-chain or branched-chain in configuration. The term "halo"—i.e., halogen—designates one of chlorine, bromine and fluorine. Preferred alkylthioalkyl, alkylsulfinylalkyl and alkylsulfonylalkyl moieties are those of the formula:

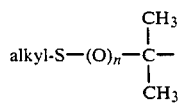

wherein n is zero, one or two. Preferably, $R^1$ is tertiary-butyl.

Compounds of Formula I wherein $X = >N—R^3$ can be prepared by treating a solution of the appropriate urea

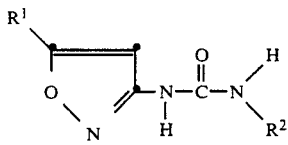
(II)

in an inert solvent with aqueous formaldehyde and treating the resulting mixture with the appropriate amine, $R^3$—$NH_2$. The reaction proceeds according to the equation:

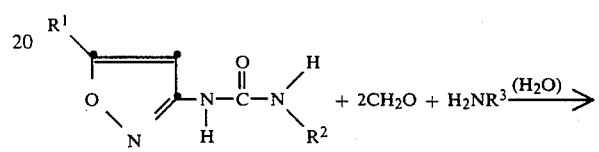

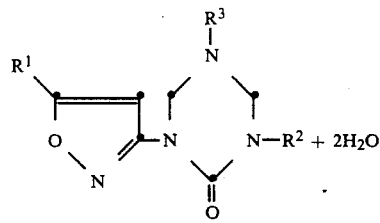

The treatment is conveniently conducted by slowly adding the formaldehyde solution to a stirred solution of the urea in the solvent, at room temperature, cooling if needed to maintain the temperature of the mixture below about 35° C., then slowly adding the amine, again cooling the mixture if needed to maintain its temperature below about 35° C. It may be found desirable to warm the mixture—for example, on a water bath, or even reflux it—after the amine has been added, to ensure completion of the reaction. Suitable solvents are aprotic liquids, such as dimethylformamide, dimethyl sulfoxide and sulfolane.

Most of the oxazolylurea precursors (Formula II) are known compounds: U.S. Pat. No. 4,062,861. Those wherein $R^3$ represents a moiety

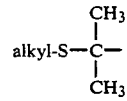

can be prepared by methods shown in that patent, the precursor amine being prepared from the nitrile, which in turn is prepared from methyl 2-methyl-2-methylthiopropionate, according to procedures described in Example 3, hereinafter. The ester can be prepared from methyl 2-bromo-2-methylpropionate (C. C. Price and E. C. Coyner, *J. Am. Chem. Soc.*, (1940) 62, 1306-7) by the procedure shown in U.S. Pat. No. 3,994,997 for the preparation of the ethyl ester.

The oxazolylamine precursor wherein $R^1$=tertiary-butyl is the subject of British Pat. No. 2,014,992. The others can be prepared by the procedures described in that patent. Preparation of particular species of the precursor amines are shown in the examples, hereinafter.

Compounds of Formula I wherein X=—O— can be prepared by treating the appropriate urea (Formula II) with paraformaldehyde in an inert solvent and in the presence of an acid, such as p-toluenesulfonic acid, as catalyst, the reaction proceeding according to the equation:

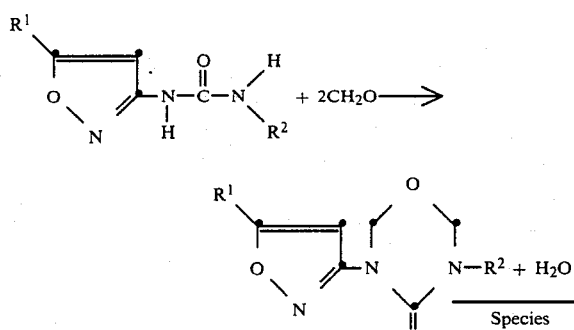

The treatment is conveniently conducted by heating a mixture of the urea, the paraformaldehyde, catalyst and solvent at a moderately elevated temperature—for example, 60°-90° C. Aromatic hydrocarbons, such as toluene, are suitable solvents. If desired, a small amount—e.g., 10-30% of the amount of the amine, on a molar basis—may be included as a promoter.

Those compounds of formula I wherein $R^3$ is the moiety

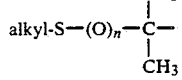

wherein n is one or two, can be prepared by conventional oxidation of the corresponding compounds of Formula I wherein n is zero. The oxidations can be effected by using such oxidizing reagents as hydrogen peroxide/acetic acid, peracids (for example, meta-chloroperbenzoic acid), sodium metaperiodate, chromic acid/acetic acid, nitric acid, or potassium permanganate/acetic acid (or acetone), as described in "Methoden der Organischen Chemie", (Houben-Weyl), Schewfel-, Selen-, und Tellur-Verbindungen, Vol. IX, pp. 207-208, Thieme Verlag, Stuttgart, Germany (1955).

The preparation, isolation and testing of three typical individual species of the compounds of Formula I are described in the examples, following. The class of compounds is further illustrated and exemplified by the following further individual species, all of which are specifically contemplated in this invention. In the interest of brevity, in the identification of these species, they are identified in terms of the substituent moieties, Formula I:

| Species No. | $R^3$ | $R^2$ | $R^1$ |
|---|---|---|---|
| X = >N—$R^3$ | | | |
| 1 | methyl | cyclopropyl | tertiary-butyl ($(CH_3)_3C-$) |
| 2 | methyl | allyl | tertiary-butyl |
| 3 | methyl | propargyl | 1-methylcyclopropyl |
| | | (CH≡C—$CH_2$—) |  $CH_3$ |
| 4 | methyl | methyl | cyclopropyl |
| 5 | methyl | methoxy | 1,1-dimethyl-2-propynyl (CH≡C—$C(CH_3)_2$—) |
| 6 | propargyl | cyclopropyl | 1,1-dimethyl-2-propynyl |
| 7 | | methyl | 1-methyl-1-methylthio-ethyl($CH_3$—S—$C(CH_3)_2$—) |
| 8 | | methyl | 1-methyl-1-methylsulfenyl-ethyl($CH_3$—S(O)—$C(CH_3)_2$—) |
| 9 | | methyl | 1-methyl-1-methylsulfonyl-ethyl($CH_3$—$S(O)_2$—$C(CH_3)_2$—) |
| X = —O— | | | |
| 10 | | cyclopropyl | tertiary-butyl |
| 11 | | methyl | 1,1-dimethyl-2-propynyl |
| 12 | | methoxy | 1,1-dimethyl-2-propynyl |
| 13 | | cyclopropyl | 1,1-dimethyl-2-propynyl |

The preparation, isolation and physical properties of typical individual species of the compounds of Formula I, in particular instances, are described in the following examples. In each case, the identity of the product, and each of any intermediate involved, was confirmed by appropriate chemical and spectral analyses.

EXAMPLE 1

3,5-Dimethyl-1-(5-(tertiary-butyl)-1,2-oxazol-3-yl)hexahydro-1,3,5-triazin-2-one (1)

A solution of 41.5 g of hydroxylamine hydrochloride in 136 ml of water was added drop-by-drop over a 10-minute period to a stirred, refluxing mixture of 56.1 g of pivaloylacetonitrile (British Pat. No. 2,014,992), 700 ml of water and 525 ml of ethanol. The mixture was held under those conditions for 7 hours, the pH of the mixture being periodically adjusted to 6.5 by the addition of either hydrogen chloride or aqueous sodium hydroxide solution, as required. Then the solvent ethanol was evaporated in a rotary evaporator, and the residual liquid was dried ($MgSO_4$), placed in 200 ml of hexane and chilled. Filtration and fractional crystallization of the solid gave 3-amino-5-(tertiarybutyl)-1,2-oxazole (1A) a yellow solid, m.p.: 107°–109° C.

1A was converted to 1-methyl-3-(5-(tertiary-butyl)-1,2-oxazol-3-yl)urea (1C) by the method and procedures disclosed in U.S. Pat. No. 4,062,861.

24 ml of a 36% aqueous formaldehyde solution was added drop-by-drop to a stirred solution of 15.0 g of 1C in 75 ml of dimethylformamide. The resulting mixture was stirred for 30 minutes, then 12 ml of a 40% aqueous methylamine solution was added drop-by-drop, the temperature of the mixture being held below 35° C. The resulting solution was stirred at room temperature for 30 minutes, then on a hot water bath for 4 hours, then the solvent was evaporated under reduced pressure. The residue was a colorless syrup that crystallized upon standing. Recrystallization from hexane gave 1, as a colorless solid, m.p.: 100°–102° C.

EXAMPLE 2

3,5-Dimethyl-1-(5-(1-(methoxymethyl)-1-methylethyl)-1,2-oxazol-3-yl)hexahydro-1,3,5-triazin-2-one (2)

219 g of chloropivaloyl chloride was added drop-by-drop to a chilled (0°–5° C.), stirred solution of 141.4 g of triethylamine in 320 g of anhydrous methanol. The resulting mixture was warmed to room temperature in one hour, and most of the methanol was evaporated under reduced pressure. The residue was drowned in water and extracted with ether. The extract was dried ($MgSO_4$) and the solvent was evaporated. The residue was distilled to give methyl 3-chloro-2,2-dimethylpropionate (2A), b.p.: 40°–50° C. (14 Torr.).

A solution of 168.3 g of 2A in 76 g of acetonitrile and 118 ml of tetrahydrofuran was added drop-by-drop over a one-hour period to a stirred, refluxing mixture of 42.2 g of sodium hydride and 766 ml of tetrahydrofuran. The resulting mixture was stirred and refluxed for 18 hours, then part of the solvent was evaporated. The residue was drowned in 1 liter of ice water, and the resulting mixture was acidified with hydrochloric acid and extracted with ether. The extract was dried ($MgSO_4$), concentrated and distilled to give ((1-(methoxymethyl)-1-methylethyl)carbonyl)acetonitrile (2B), as a colorless liquid, b.p.: 86°–90° C. (0.2 Torr.).

A solution of 58.5 g of hydroxylamine hydrochloride in 88 ml of water was added drop-by-drop over a 10-minute period to a stirred, refluxing solution of 100.9 g of 2B and 33.7 g of sodium hydroxide in 950 ml of water and 740 ml of ethanol. The mixture was stirred and refluxed for a further 18 hours, then the ethanol was evaporated in a rotary evaporator. The aqueous residue was cooled and filtered. The solid was chromatographed over silica gel, using as eluent a 2:15:33 v:v:v mixture of tetrahydrofuran, ethyl acetate and hexane, to give 3-amino-5-(1-(methoxymethyl)-1-methylethyl)-1,2-oxazole (2C), as a cream-colored solid, m.p.: 96°–99° C.

2C was converted to 1-methyl-3-(5-(1-(methoxymethyl)-1-methylethyl)-1,2-oxazol-3-yl)urea (2D), as a solid, m.p.: 113°–115° C., by the procedures described in U.S. Pat. No. 4,062,861.

16 ml of a 36% aqueous formaldehyde solution was added dropwise to a stirred solution of 4.1 g of 2D in 75 ml of dimethylformamide. The temperature of the mixture rose from 22° C. to 27° C. The mixture was stirred for 30 minutes, then 8 ml of a 40% solution of methylamine in water was added, drop-by-drop. The temperature of the mixture rose from 27° C. to 36° C. The mixture was refluxed for 3 hours, then the solvent was evaporated under reduced pressure. The residue was mixed with cold water, and the resulting mixture was extracted with ether. The solvent was evaporated from the extract, and the residue was crystallized when hexane was added, to give 2, as a white solid, m.p.: 49°–50° C.

EXAMPLE 3

3,5-Dimethyl-1-(5-(1,1-dimethyl-2-propynyl)-1,2-oxazol-3-yl)-hexahydro-1,3,5-triazin-2-one (3)

The methyl ester of 2,2-dimethyl-3-butynoic acid (3A) was prepared from the acid (M. A. Schexnayder and P. S. Engel, Journal of the American Chemical Society, Vol. 97, pp 4825 et seq. (1975)) by conventional procedures.

A mixture of 109.8 g of 3A and 56.2 g of acetonitrile was added drop-by-drop to a stirred, refluxing mixture of 72.5 g of sodium hydride and 650 ml of tetrahydrofuran. The mixture was stirred and refluxed for 2 hours, then cooled to 20° C. and stirred for 18 hours. Then the solvent was evaporated in a rotary evaporator, the residue was drowned in 500 ml of ether, and water was added cautiously. The resulting aqueous phase was separated, acidified with hydrochloric acid and extracted with ether. The extract was dried ($MgSO_4$) and the solvent was evaporated. The residue, a dark viscous syrup, was distilled to give ((1,1-dimethyl-2-propyn-1-yl)carbonyl)acetonitrile (3B), a yellow liquid, b.p.: 65°–67° C. (0.5 Torr.).

Over a 15-minute period, 21.0 g of 3B was added to a solution of 9.1 g of sodium hydroxide in 240 ml of water and 200 ml of ethanol at room temperature. The pH of the mixture was adjusted to 6.4–6.6. The mixture was stirred, heated to 90° C. and stirred at that temperature for 8 hours. The ethanol was evaporated under reduced pressure and the aqueous residue was extracted with ether. The extract was dried ($MgSO_4$) and concentrated. The resulting amber syrup was chromatographed over silica gel, using Solvent No. 3 as eluent, to give 3-amino-5-(1,1-dimethyl-2-propyn-1-yl)-1,2-oxazole (3C), as an off-white solid, m.p.: 98°–100° C.

A solution of 7.5 g of 3C and 5 ml of methyl isocyanate in 50 ml of tetrahydrofuran was heated at 50°–60° C. for two days. The solvent was evaporated under reduced pressure and the residue was chromatographed over silica gel, using as eluent a 1:4:20 v:v:v mixture of tetrahydrofuran, ethyl acetate and hexane, to give 1-methyl-3-(5-(1,1-dimethyl-2-propyn-1-yl)-1,2-oxazol-3-yl)urea (3D), as a white crystalline solid, m.p.: 99°–100° C.

3 ml of a 36% aqueous formaldehyde solution was added drop-by-drop to a stirred solution of 1.0 g of 3D in 25 ml of dimethylformamide, at room temperature. After 30 minutes of stirring, 1.5 ml of 40% aqueous methylamine solution was added drop-by-drop, to the mixture. The resulting mixture was stirred for 30 minutes at room temperature and then on a water bath for one hour, then was held at room temperature for 18 hours. The solvents were evaporated under reduced pressure in a rotary evaporator. The residue was chromatographed over silica gel, using as eluent a 2:15:13 v:v:v mixture of tetrahydrofuran, ethyl acetate and hexane, to give 3, as a colorless solid, m.p.: 85°–87° C., upon recrystallization from ether.

EXAMPLE 4

5-methyl-3-methoxy-1-(5-(tetiary-butyl)-1,2-oxazol-3-yl)hexahydro-1,3,5-triazin-2-one (4)

99 g of phosgene was bubbled into 500 ml of ethyl acetate, then a solution of 71.6 g of 1A in 400 ml of ethyl acetate was added drop-by-drop to the stirred mixture. The mixture was stirred at reflux temperature for five hours, left standing overnight at room temperature, and filtered. The solid was dried at room temperature for two days to give dimeric 3-isocyanato-5-(tertiary-butyl)-1,2-oxazole (4A), m.p.: 165°–167° C.

8.5 g of methoxyamine was added very slowly to a stirred solution of 15 g of 4A in 600 ml of tetrahydrofuran. The resulting mixture was filtered and the solid was triturated with ether to give 1-methoxy-3-(5-(tertiary-butyl)-1,2-oxazol-3-yl)urea (4B), m.p.: 145°–148° C.

By the procedure described in the last paragraph of Example 1, 4B was converted to 4, which was isolated as a solid, m.p.: 90°–92° C., by chromatographing the crude reaction product over silica gel, using a 1:1:2 v:v:v mixture of tetrahydrofuran, ethyl acetate and hexane as eluent, 4 being the first fraction collected.

EXAMPLE 5

3-Methyl-5-(5-tertiary-butyl)-1,2-oxazol-3-yl)-2,6-dihydro-1,3,5-oxadiazin-4-one (5)

A mixture of 5.0 g of 1C, 0.75 g of paraformaldehyde, 1.3 g of para-toluenesulfonic acid, 0.51 g of dimethylformamide and 150 ml of toluene was stirred at 80° C. for 15 minutes. The resulting mixture was poured into 200 ml of water and phase-separated. The toluene phase was dried (MgSO$_4$), filtered and concentrated in a rotary evaporator. The residue was triturated with hexane, and the liquid was chromatographed over silica gel, using a 20:4:1 v:v:v mixture of hexane, ethyl acetate and tetrahydrofuran as eluent. Workup gave 5, as a colorless syrupy liquid.

Compounds of Formula I have been found to adversely affect the growth of plants, many of which are commonly considered as weeds, and therefore to be useful for controlling the growth of such unwanted plants. Compounds of Formula I have been found to have selectivity with respect to some crop plants—i.e., they control weeds at dosages at which they do not significantly harm the crop plants. Compounds of Formula I appear to be effective when applied preemergence or preplant incorporated (applied to the soil before the seeds have sprouted) or when applied postemergence (applied to the foliage of the growing plant). Some appear to be somewhat more effective when applied preemergence than when applied postemergence.

Accordingly, the invention includes a method of combatting unwanted plants which comprises applying to the locus an effective amount of a compound of Formula I. In the cases where it is desired to control weeds in crop plantings, it is of course preferable to employ the lowest dosage that will control the weeds, for this will minimize any possible deleterious effect of the compound upon the crop plants. For application, the compound generally is applied most effectively by formulating it with a suitable inert carrier or surface-active agent, or both. The invention, therefore, also includes compositions suitable for combatting unwanted plants, such compositions comprising an inert carrier or surface-active agent, or both, and as active ingredient at least one compound of formula I.

The term "carrier" as used herein means an inert solid or fluid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides, herbicides, or fungicides, are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable fluid carriers are water, alcohols such as, for example, isopropyl alcohol, glycols; ketones such as, for example, acetone, methyl ethyl ketone, methyl isobutyl ketone and cyclohexanone; ethers such as, for example, cellosolves; aromatic hydrocarbons such as, for example, benzene, toluene and xylene; petroleum fractions such as, for example, kerosene, light mineral oils; chlorinated hydrocarbons such as, for example, carbon tetrachloride, perchloroethylene, trichloroethane, including liquefied, normally vaporous, gaseous compounds. Mixtures of different liquids are often suitable.

The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkyl-aryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25, 50 or 75% by weight of the active compound and usually contain, in addition to the solid carrier, 3-10% by weight of a dispersing agent, 15% of a surface-active agent and, where necessary, 0-10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5-10% by weight of the active compound. Granules are usually prepared to have a size between 10 and 100 BS mesh (1.676-0.152 mm), and may be manufactured by agglomeration or impregnation techniques. Generally, granules will contain 0.5-25% by weight of the active compound, 0-1% by weight of additives such as stabilizers, slow release modifiers and binding agents. Emulsifiable concentrates usually contain, in addition to the solvent and, when necessary, cosolvent, 10-50% weight per volume of the active compound, 2-20% weight per volume emulsifiers and 0-20% weight per volume of appropriate additives such as stabilizers, penetrants and corrosion inhibitors. Suspension concentrates are compounded so as to obtain a stable, non-sedimenting, flowable product and usually contain 10-75% weight of the active compound, 0.5-5% weight of dispersing agents, 1-5% of surface-active agent, 0.1-10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick, mayonnaise-like consistency.

The compositions of the invention may also contain other ingredients, for example, other compounds possessing pesticidal, especially insecticidal, acaricidal, herbicidal or fungicidal properties, as are appropriate to the intended purpose.

Protection of a locus or area from undesirable plants is effected by applying a compound of Formula I, ordinarily in a composition of one of the aforementioned types, to soil in which the seeds of the unwanted plants are present, or to the foliage of the unwanted plants. The active compound, of course, is applied in an amount sufficient to exert the desired action.

The amount of the compound of the invention to be used in combatting undesired plants will naturally depend on the condition of the plants, the degree of activity desired, the formulation used, the mode of application, the climate, the season of the year, and other variables. Recommendations as to precise amounts are, therefore, not possible. In general, however, application to the locus to be protected of from 0.1 to 10.0 kg per hectare of the compound of Formula I will be satisfactory.

EXAMPLES OF ACTIVITY WITH RESPECT TO PLANTS

In the following examples, the species of plants that were tested were:
Barnyardgrass (watergrass)—*Enchinochloa crus-galli*
Large crabgrass—*Digitaria sanguinalis*
Downy brome—*Bromus tectorum*
Yellow foxtail—*Setaria lutescens*
Redroot pigweed—*Amaranthus retroflexus*
Sicklepod—*Cassia obtusifolia*
Velvetleaf—*Abutilon theophrasti*
Garden cress—*Lepidium sativum*
Johnsongrass—*Sorghum halepense*

Test Procedures

The preemergence (soil) herbicidal activity of the compounds was evaluated by planting seeds of barnyardgrass, garden cress, downy brome, velvetleaf, yellow foxtail, and sicklepod in test tubes, nominally measuring 25×200 millimeters, filled about three-quarters full of untreated soil, in each case covered on top with about 2.5 cubic centimeters of soil treated with a certain amount of the test compound. The treated soil applied to the tubes containing the barnyardgrass and cress seeds contained one milligram of the test compound per tube, and contained 0.1 milligram of the test compound per each tube containing the seeds of the other plants. The dosages were approximately 20 and 2.0 pounds of test compound per acre, respectively. The seeds were planted on top of the treated soil and covered with about 1.5 cubic centimeters of untreated soil. The planted soil was held under controlled conditions of temperature, moisture, and light for 9 to 10 days. The amounts of germination and growth in each tube were evaluated on a 0 to 9 scale, the numeric ratings having the following meanings:

| Rating | Meaning |
| --- | --- |
| 9 | No living tissue |
| 8 | Plant severely damaged and expected to die |
| 7 | Plant badly damaged, but expected to live |
| 6 | Moderate damage, but complete recovery expected |
| 5 | Intermediate damage (probably unacceptable for crop plants) |
| 3-4 | Observable damage |
| 1-2 | Plant slightly affected, possibly by the chemical, possibly due to biological variability |
| 0 | No visible effect |

The postemergence (foliar) herbicidal activity of compounds of the invention was evaluated by spraying 10-day-old large downy brome plants in some cases, 6-day-old Johnsongrass plants in other cases, 9-day-old velvetleaf plants, 9-day-old yellow foxtail plants and 9-day-old sicklepod plants to runoff with a liquid formulation of the test compound. The crabgrass and pigweed plants were sprayed with 2.4 milliliters of a 0.25% solution (about ten pounds of the test compound per acre), and other plants were sprayed with 2.5 milliliters of a 0.025% solution (about one pound of the test compound per acre). The sprayed plants were held under controlled conditions of temperature, moisture and light for 7 to 8 days, and the effect of the test compound was then evaluated visually, the results being rated on the 0 to 9 scale described above.

Results of the preemergence and postemergence herbicidal activity tests are set forth in Table I.

TABLE I

| | HERBICIDAL ACTIVITY | | | | | | | | | | | |
|---|---|---|---|---|---|---|---|---|---|---|---|---|
| | Preemergence | | | | | | Postemergence | | | | | |
| Compound | Barnyard grass | Garden Cress | Downy Brome | Velvet-leaf | Yellow Foxtail | Sickle-pod | Crab-grass | Pig-weed | Johnson-grass | Velvet-leaf | Yellow Foxtail | Sickle-pod |
| 1 | 9 | 9 | 6 | 9 | 8 | 9 | 9 | 9 | 2 | 8 | 4 | 8 |
| 2 | 9 | 9 | 3 | 8 | 6 | 8 | — | 5 | 0 | 3 | 2 | 4 |
| 3 | 8 | 9 | 6 | 9 | 8 | 9 | 6 | 8 | 2 | 7 | 5 | 7 |
| 4 | 8 | 7 | 2 | 6 | 5 | 6 | 2 | 6 | 0 | 4 | 0 | 5 |
| 5 | 9 | 9 | 8 | 9 | 9 | 9 | 9 | 9 | 5 | 6 | 4 | 7 |

EXAMPLES OF SELECTIVITY

In the following examples, the species of plants that were tested were:
Barnyardgrass
Downy brome
Johnsongrass
Wild oats—*Avena fatua*
Yellow foxtail
Goose grass—*Eleusine indica* L.
Yellow nutsedge—*Cyperus esculentus* L.
Cocklebur—*Xanthum pennsylvanicum*
Morning glory—*Ipomoea purpurea* L. (Roth)
Wild mustard—*Brassica kaber*
Redroot pigweed
Sicklepod
Velvetleaf
Corn—*Zea mays*
Cotton—*Gossypium hirsutum*
Rice—*Oryza sativa*
Grain sorghum—*Sorghum vulgare*
Soybeans—*Glycine max*
Sugarbeets—*Beta vulgaris*
Wheat—*Triticum aestivum*

Test Procedures

The preemergence activity of Compound (1) was further determined with respect to certain species of crop plants and common species of weeds, by spraying a formulation of the test compound on soil in small pots in which seeds of the plants had been sown. The results of the tests were evaluated on the basis of the 0–9 scale described with respect to the earlier tests. The results of the tests are reported in Table II.

TABLE II

| | COMPOUND 1 | |
|---|---|---|
| | Rating of Effect at Indicated Dosage (lb/acre) Preemergence | |
| Plant Species | 0.25 | 0.0625 |
| Corn | 0 | 0 |
| Cotton | 0 | 0 |
| Rice | 9 | 5 |
| Grain Sorghum | 6 | 0 |
| Soybean | 8 | 2 |
| Sugar Beet | 9 | 9 |
| Wheat | 9 | 7 |
| Barnyard Grass | 8 | 0 |
| Downy Brome | 3 | 0 |
| Johnsongrass | 7 | 0 |
| Wild Oats | 9 | 0 |
| Yellow Foxtail | 9 | 0 |
| Goose grass | 8 | 0 |
| Yellow Nutsedge | 0 | 0 |
| Cocklebur | 9 | 0 |
| Morning Glory | 9 | 7 |
| Mustard | 9 | 5 |
| Pigweed | 9 | 5 |
| Sicklepod | 9 | 0 |
| Velvetleaf | 9 | 3 |

I claim:
1. A compound of the formula

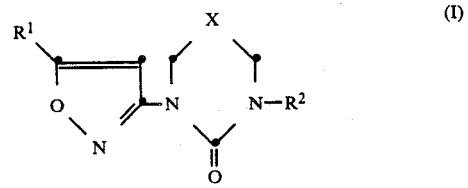

wherein $R^1$ contains from three to five carbon atoms and is one of alkyl, alkenyl, alkynyl, alkoxyalkyl, alkylthioalkyl, alkylsulfinylalkyl, alkylsulfonylalkyl, cycloalkyl, and alkylcycloalkyl, $R^2$ is alkyl, alkoxy, (mono- or polyhalo)alkyl of from one to three carbon atoms, cycloalkyl of from three to six carbon atoms, or alkenyl of from three to five carbon atoms, and X is —O— or $$-\overset{R^3}{\underset{|}{N}}-,$$

wherein $R^3$ is alkyl of from one to three carbon atoms, cyclopropyl or 1-methylcyclopropyl.

2. A compound according to claim 1 wherein $R^1$ is tertiarybutyl, $R^2$ is methyl.

3. A compound according to claim 1 wherein $X=>N—R^3$, wherein $R^1$ is tertiary butyl, $R^2$ is methyl and $R^3$ is methyl.

4. A plant growth inhibiting composition which comprises a plant growth inhibiting effective amount of a compound of claim 1 and an inert carrier, a surface-active agent, or both.

5. A composition according to claim 4 wherein $R^1$ is tertiarybutyl, $R^2$ is methyl and $R^3$ is methyl.

6. A method for inhibiting the growth of unwanted plants at a locus which comprises applying to the locus a plant growth inhibiting effective amount of a compound of claim 1.

7. A method for inhibiting the growth of unwanted plants at a locus which comprises applying to the locus a plant growth inhibiting effective amount of a compound of claim 2.

* * * * *